(12) United States Patent
Tschirschwitz et al.

(10) Patent No.: US 10,081,580 B2
(45) Date of Patent: Sep. 25, 2018

(54) PROCESS FOR PREPARING CYCLOHEXANE WITH STARTING MATERIALS ORIGINATING FROM A STEAMCRACKING PROCESS

(71) Applicant: BASF SE, Ludwingshafen (DE)

(72) Inventors: Steffen Tschirschwitz, Mannheim (DE); Kathrin Wissel-Stoll, Ludwigshafen (DE); Jochen Bürkle, Mannheim (DE); Albena Kostova, Mannheim (DE); Markus Schmitt, Heidelberg (DE); Veronika Wloka, Mannheim (DE); Stephan Deuerlein, Ludwigshafen (DE); Marco Bosch, Lampertheim (DE); Steffen Oehlenschläger, Bad Dürkheim (DE); Michael Schreiber, Mannheim (DE); Gauthier Luc Maurice Averlant, Frankfurt (DE); Joni Joni, Sulzbach (DE); Roman Prochazka, Mannheim (DE); Martin Bock, Ludwigshafen (DE); Alois Kindler, Grünstadt (DE); Daniela Malkowsky, Speyer (DE); Katharina Spuhl, Forest (BE); Stefan Bitterlich, Dirmstein (DE); Daniel Pfeiffer, Neustadt (DE)

(73) Assignee: BASF SE, Ludwigshafen am Rhein (DE)

( * ) Notice: Subject to any disclaimer, the term of this patent is extended or adjusted under 35 U.S.C. 154(b) by 464 days.

(21) Appl. No.: 14/053,634

(22) Filed: Oct. 15, 2013

(65) Prior Publication Data
US 2014/0114099 A1    Apr. 24, 2014

Related U.S. Application Data

(60) Provisional application No. 61/715,311, filed on Oct. 18, 2012.

(51) Int. Cl.
*C07C 5/29*    (2006.01)
*C07C 5/10*    (2006.01)
(Continued)

(52) U.S. Cl.
CPC .............. *C07C 5/29* (2013.01); *C07C 5/10* (2013.01); *C07C 7/08* (2013.01); *C07C 7/163* (2013.01);
(Continued)

(58) Field of Classification Search
CPC .. C07C 5/10; C07C 13/18; C07C 5/29; C07C 7/08; C07C 7/163
See application file for complete search history.

(56) References Cited

U.S. PATENT DOCUMENTS 2,846,485 A    8/1958  Meason et al.
3,009,002 A *  11/1961 Kron ...................... C07C 7/005
                                                   208/64
(Continued)

FOREIGN PATENT DOCUMENTS

CN    101448768 A    6/2009
EP       1127601 A2   8/2001
(Continued)

OTHER PUBLICATIONS

Bajus "Steam Cracking of Hydrocarbons. 3. Straight-Run Naphtha." Ind. Eng. Chem. Prod. Res. Dev., vol. 19, No. 4, 1980, 556-563).*

(Continued)

*Primary Examiner* — Brian A McCaig
*Assistant Examiner* — Jason Y Chong
(74) *Attorney, Agent, or Firm* — Drinker Biddle & Reath LLP

(57) ABSTRACT

The present invention relates to a process for preparing cyclohexane by isomerizing a hydrocarbon mixture (HM1) comprising methylcyclopentane (MCP) in the presence of a catalyst. The catalyst is preferably an acidic ionic liquid. The starting material used is a stream (S1) which originates from a steamcracking process. The hydrocarbon mixture (HM1) obtained from this stream (S1) in an apparatus for aromatics removal has a reduced aromatics content compared to stream (S1), and (HM1) may optionally also be (virtually) free of aromatics. Depending on the type and amount of the (Continued)

aromatics remaining in the hydrocarbon mixture (HM1), especially in the case that benzene is present, the isomerization may additionally be preceded by performance of a hydrogenation of (HM1). In addition, depending on the presence of other components of (HM1), further purification steps may optionally be performed prior to or after the isomerization or hydrogenation. High-purity (on-spec) cyclohexane is preferably isolated from the hydrocarbon mixture (HM2) obtained in the isomerization, the specifications being, for example, those applicable to the use of the cyclohexane for the preparation, known to those skilled in the art, of caprolactam.

28 Claims, 3 Drawing Sheets

(51) Int. Cl.
    *C07C 7/08*    (2006.01)
    *C07C 7/163*   (2006.01)
(52) U.S. Cl.
    CPC ...... *C07C 2521/04* (2013.01); *C07C 2521/06* (2013.01); *C07C 2521/08* (2013.01); *C07C 2523/46* (2013.01); *C07C 2523/745* (2013.01); *C07C 2523/75* (2013.01); *C07C 2523/755* (2013.01); *C07C 2527/11* (2013.01); *C07C 2527/125* (2013.01); *C07C 2527/1206* (2013.01); *C07C 2527/126* (2013.01); *C07C 2527/1213* (2013.01); *C07C 2527/135* (2013.01); *C07C 2601/14* (2017.05)

(56) References Cited

U.S. PATENT DOCUMENTS

| | | | |
|---|---|---|---|
| 3,311,667 A | 3/1967 | Cabbage | |
| 3,406,217 A | 10/1968 | Davison et al. | |
| 4,053,369 A | 10/1977 | Cines | |
| 4,097,371 A * | 6/1978 | Giroux | C07C 7/08 203/81 |
| 4,955,468 A | 9/1990 | Lee | |
| 6,177,600 B1 * | 1/2001 | Netzer | C07C 11/04 585/323 |
| 6,503,465 B1 | 1/2003 | Lin et al. | |
| 7,645,808 B2 * | 1/2010 | Dierickx | C07C 4/02 518/700 |
| 7,932,427 B2 | 4/2011 | Chewter et al. | |
| 2003/0109767 A1 | 6/2003 | Vasina et al. | |
| 2005/0082201 A1 | 4/2005 | Groten et al. | |
| 2011/0137097 A1 | 6/2011 | Tschirschwitz et al. | |
| 2011/0137098 A1 | 6/2011 | Tschirschwitz et al. | |
| 2011/0139604 A1 | 6/2011 | Burst et al. | |

FOREIGN PATENT DOCUMENTS

| | | | |
|---|---|---|---|
| EP | 1403236 A1 | 3/2004 | |
| EP | 1992673 A1 | 11/2008 | |
| EP | 1995297 A1 | 11/2008 | |
| WO | WO-2002022528 A1 | 3/2002 | |
| WO | WO-2010027987 A2 | 3/2010 | |
| WO | WO-2010074836 A2 | 7/2010 | |
| WO | WO-2011069929 A1 | 6/2011 | |
| WO | WO-2011069957 A1 | 6/2011 | |

OTHER PUBLICATIONS

U.S. Appl. No. 61/715,308.
U.S. Appl. No. 61/715,306.
U.S. Appl. No. 61/670,134.
U.S. Appl. No. 61/670,131.
U.S. Appl. No. 61/670,136.
U.S. Appl. No. 61/670,130.
U.S. Appl. No. 61/670,140.
U.S. Appl. No. 61/670,142.
U.S. Appl. No. 61/670,133.
U.S. Appl. No. 61/670,135.
U.S. Appl. No. 61/670,132.
Kirk-Othmer Encyclopedia of Chemical Technology, vol. 8, (2001), pp. 739-785.

* cited by examiner

PROCESS FOR PREPARING CYCLOHEXANE WITH STARTING MATERIALS ORIGINATING FROM A STEAMCRACKING PROCESS

This patent application claims the benefit of U.S. provisional patent application Ser. No. 61/715,311 filed on Oct. 18, 2012, incorporated in its entirety herein by reference.

The present invention relates to a process for preparing cyclohexane by isomerizing a hydrocarbon mixture (HM1) comprising methylcyclopentane (MCP) in the presence of a catalyst. The catalyst is preferably an acidic ionic liquid. The starting material used is a stream (S1) which originates from a steamcracking process. The hydrocarbon mixture (HM1) obtained from this stream (S1) in an apparatus for aromatics removal, preferably benzene removal, has a reduced aromatics content compared to stream (S1), and (HM1) may optionally also be (virtually) free of aromatics. Depending on the type and amount of the aromatics remaining in the hydrocarbon mixture (HM1), especially in the case that benzene is present, the isomerization may additionally be preceded by performance of a hydrogenation of (HM1). In addition, depending on the presence of other components of (HM1), further purification steps may optionally be performed prior to or after the isomerization or hydrogenation. High-purity (on-spec) cyclohexane is preferably isolated from the hydrocarbon mixture (HM2) obtained in the isomerization, the specifications being, for example, those applicable to the use of the cyclohexane for the preparation, known to those skilled in the art, of caprolactam.

Cyclohexane is an important product of value in the chemical industry, which is preferably prepared by hydrogenation of benzene provided in substantially pure form. However, the problem arises that benzene is a scarce product and therefore hydrogenation to cyclohexane competes with other uses, for example the preparation of styrene. There is therefore an incentive to find a preparation process for cyclohexane which proceeds from a feedstock other than pure benzene.

A steamcracking process is generally understood to mean a petrochemical process which has been known for some time and in which principally longer-chain hydrocarbons are converted to short-chain hydrocarbons in the presence of steam by thermal cracking. The longer-chain hydrocarbons used as the starting material are especially naphtha obtained in a mineral oil refinery, but it is additionally also possible to use light hydrocarbon fractions from accompanying gases in oil production or heavy fractions ("C2+") separated from natural gas. The hydrocarbon mixture (HM1) used in the context of the present invention originates preferably from a steamcracking process in which predominantly naphtha is used as a feedstock ("naphtha cracker"). The products formed in a steamcracking process are particularly hydrogen, methane, short-chain hydrocarbons such as ethene, propene and butenes, and aromatics-containing pyrolysis gasoline (comprising, among other substances, benzene and toluene and other hydrocarbons, for example linear, branched or cyclic $C_5$-$C_6$-alkanes such as MCP).

The pyrolysis gasoline obtained in a steamcracking process is generally, optionally after a low boiler removal and/or the removal of a fraction enriched in C9 hydrocarbons, subjected to a distillative separation into various fractions, preferably in each case a fraction enriched in benzene, one enriched in toluene and one enriched in xylenes. This sequence is optionally supplemented by one or more selective hydrogenations for the purpose of converting olefins and/or dienes and/or olefinic side groups of aromatics and/or sulfur compounds.

It is additionally known that cyclohexane can be prepared not only by hydrogenation of benzene, as described above, but also by isomerization of MCP. The catalysts used for such an isomerization are preferably acidic catalysts in the form of a Lewis or Brønsted acid, for example Friedel-Crafts catalysts or else acidic ionic liquids.

US-A 2003/0109767 discloses a process for isomerizing $C_5$-$C_8$ paraffin hydrocarbons (paraffins) in the presence of an ionic liquid as a catalyst. The ionic liquid comprises, as cations, nitrogen-containing heterocycles or nitrogen-containing aliphatics; the corresponding anions are derived from metal halides. The paraffins to be isomerized are linear alkanes such as n-hexane or n-octane and monosubstituted alkanes such as 3-methylhexane or mixtures thereof. The process described in US-A 2003/0109767 is intended to prepare paraffins having a relatively high degree of branching. In contrast, cyclohexane, for example, has a lower degree of branching compared to MCP. Moreover, US-A 2003/0109767 does not make any statements as to where the hydrocarbons used for isomerization come from or that the starting mixture is used to perform an aromatics removal or any remaining aromatics are optionally hydrogenated prior to the isomerization.

In the isomerization process described in EP-A 1 403 236, the intention is likewise to obtain a relatively high degree of branching in the paraffins (hydrocarbons) to be isomerized in the presence of an ionic liquid. The isomerization process is additionally performed in the presence of cyclic hydrocarbons as additives and in a reaction medium, the cyclic hydrocarbons comprising a tertiary carbon atom as a structural unit, or being converted by the reaction medium to a corresponding compound having such a structural unit. Preference is given to using methylcyclohexane or dimethylcyclopentane as such cyclic hydrocarbon additives. The paraffins to be isomerized are linear alkanes such as n-butane or n-octane, and monomethyl-substituted alkanes such as 2-methylhexane. The ionic liquids are preferably based on nitrogen-containing heterocycles or nitrogen-containing aliphatics as cations, and on inorganic anions such as haloaluminates. EP-A 1 403 236 likewise does not make any statements as to where the hydrocarbons used for isomerization come from or that the starting mixture is used to perform an aromatics removal or any remaining aromatics are optionally hydrogenated prior to the isomerization.

US-A 2005/0082201 discloses a process for, preparing gasoline with a low benzene content, wherein, in a first process step, a hydrocarbon mixture comprising benzene, olefins and sulfur compounds such as thiophenes is first fed into a distillation column, from which the low-boiling compounds are removed via the top, a benzene-containing fraction via a side draw and the high boilers from the column bottom. In a second process stage, the fraction obtained from the side draw is hydrogenated in the presence of a hydrogenation catalyst, converting benzene to cyclohexane and the thiophenes to hydrogen sulfide. The cyclohexane-containing mixture obtained in the second process stage is suitable for preparation of gasoline having a low benzene content. No isolation of the cyclohexane present therein, or an isomerization in general, for example of MCP to cyclohexane, is disclosed in US-A 2005/0082201.

WO 2010/027987 relates to a further process for reducing the concentration of benzene in a hydrocarbonaceous mixture. In a first separation stage, a benzene-containing fraction comprising benzene and other $C_6$ hydrocarbons is separated from a high boiler fraction comprising carbons having seven or more carbon atoms. The benzene-containing fraction is subsequently hydrogenated to obtain a hydrocarbon fraction having a reduced benzene content. The hydrogenation of benzene forms cyclohexane. WO 2010/027987 also does not contain any pointers that cyclohexane can be isolated from the mixture obtained in the hydrogenation; instead, this process product too is to be used for gasoline production. This document likewise does not disclose isomerization, for example of MCP to cyclohexane.

U.S. Pat. No. 3,311,667 relates to a process for removing benzene from a mixture which is subsequently fed into an isomerization of MCP to cyclohexane. The hydrogenation involves hydrogenating benzene in the presence of a suitable catalyst, for example a metal catalyst on kieselguhr, with hydrogen to cyclohexane. The isomerization of MCP to cyclohexane is performed in the presence of metal halides such as acid-enhanced aluminum halide. U.S. Pat. No. 3,311,667, however, does not describe where the hydrocarbons used for isomerization come from, or state that the starting mixture is used to perform an aromatics removal. It is likewise not disclosed therein that isomerization can also be accomplished using an acidic ionic liquid.

EP-A 1 995 297 discloses a process and a corresponding apparatus for hydrogenation and decyclization of benzene and the isomerization of $C_5$-$C_6$ paraffins present in a mixture comprising at most 1% by weight of benzene. For hydrogenation of benzene, metallic catalysts can be used, suitable metals being the elements of the platinum group, tin or cobalt and molybdenum. For isomerization of the mixture obtained in the hydrogenation, which may comprise a residual amount of benzene, zeolites in particular are used as the catalyst. In the process described in EP-A 1 995 297, the parameters in the isomerization are adjusted such that opening of the cyclohexane rings obtained in the benzene hydrogenation to isoalkanes is achieved. The primary purpose of this process is thus not the preparation of cyclohexane but the preparation of alkanes having a high degree of branching. In addition, EP-A 1 995 297 also does not contain any statements that an acidic ionic liquid can also be used for isomerization, or where the hydrocarbons used for isomerization come from, or that the starting mixture is used to perform an aromatics removal. A similar process to EP-A 1 995 297 is described in EP-A 1 992 673.

U.S. Pat. No. 2,846,485 discloses a process for preparing high-purity cyclohexane and benzene, using a mixture comprising n-hexane, benzene, MCP, cyclohexane and dimethylpentanes (DMP). In a first extractive distillation zone, benzene is separated from the other reactant components. The reactant which has been substantially freed of benzene is combined with a mixture which comprises cyclohexane and MCP and originates from the bottom of a second fractionating distillation zone. The mixture thus combined is fed into a first fractionating distillation zone, with removal of an MCP-containing fraction via the top and a cyclohexane-containing fraction from the bottom.

The overhead product of the first fractionating distillation zone is first conducted into an isomerization zone in which the majority of MCP is isomerized to cyclohexane using Friedel-Crafts catalysts such as aluminum chloride which may additionally comprise HCl. The isomerization product is introduced into the above-described second fractionating distillation zone, in order to remove n-hexane and low boilers as the top product therein. The bottom product from the first fractionating distillation zone is transferred into a second extractive distillation zone in which a cyclohexane-comprising mixture from the bottom is separated from the DMP drawn off via the top.

The process described in U.S. Pat. No. 2,846,485 is disadvantageous, since it is very complex in terms of apparatus (among other aspects). Cyclohexane, the actual process product, is not separated from DMP until the end of the process, since the cyclohexane formed in the isomerization of MCP is recycled into a DMP-containing fraction. Moreover, U.S. Pat. No. 2,846,485 does not make any statements as to where the hydrocarbons used for isomerization come from or that aromatics present in the starting mixture are optionally hydrogenated prior to the isomerization.

Ionic liquids are suitable, inter alia, as catalysts for the isomerization of hydrocarbons. A corresponding use of an ionic liquid is described, for example, in WO 2011/069929, where a specific selection of ionic liquids is used in the presence of an olefin for isomerization of saturated hydrocarbons, more particularly for isomerization of methylcyclopentane (MCP) to cyclohexane. A similar process is described in WO 2011/069957, but the isomerization therein is not effected in the presence of an olefin, but with a copper(II) compound.

It is an object of the present invention to provide a novel process for preparing cyclohexane from starting materials originating from a steamcracking process. These starting materials always comprise MCP; otherwise, they may vary in terms of their other components. In addition, it is to be possible to recover any cyclohexane present in the starting materials.

The object is achieved by a process for preparing cyclohexane, comprising the following steps:
a) isomerizing a hydrocarbon mixture (HM1) comprising methylcyclopentane (MCP) in the presence of a catalyst to obtain a hydrocarbon mixture (HM2) comprising cyclohexane,
  (HM1) being obtained in an apparatus for aromatics removal, preferably for benzene removal, connected downstream of a steamcracking process, from a stream (S1) originating from the steamcracking process, and
b) isolating cyclohexane from the hydrocarbon mixture (HM2).

A BRIEF DESCRIPTION OF THE FIGURES

DETAILED DESCRIPTION OF THE INVENTION

Figure 1:
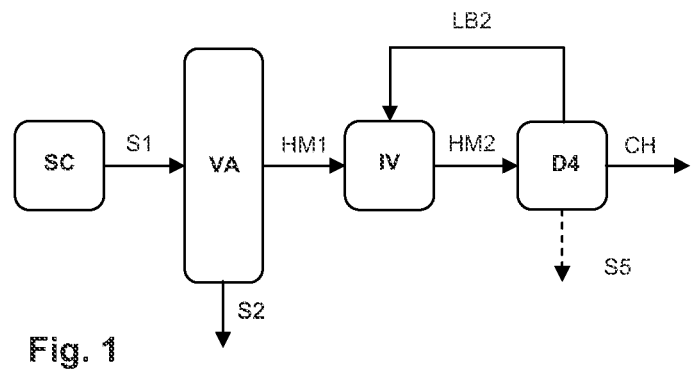
FIG. 1 shows an exemplary process according to the invention in its basic form, including steps a) and b).

The process according to the invention advantageously allows preparation of pure, especially high-purity (on-spec), cyclohexane, the specifications being, for example, those applicable to the use of the cyclohexane for the preparation, known to those skilled in the art, of caprolactam. The process according to the invention is advantageous in terms of apparatus complexity; it is additionally possible to obtain high yields of cyclohexane.

A further important advantage of the process according to the invention is considered to be that it can be performed very flexibly. According to the composition of the hydrocarbon mixture (HM1) used, the isomerization in step a) may be preceded by the performance of different intermediate steps (for example purification steps), individually or in any desired combinations. If high boilers, especially DMP, are present in (HM1), these can be completely or at least substantially separated from (HM1) prior to the isomerization and optionally also prior to the hydrogenation ("prior high boiler or DMP removal"). In addition, performance of a hydrogenation is required only if (HM1) comprises aromatics (to a significant extent), especially benzene and possibly cyclohexene. If (HM1) comprises low boilers, these can likewise be removed at a suitable point prior to the isomerization.

The specific (additional) advantages associated with the above process variants (embodiments) of the present invention are illustrated once again hereinafter. If individual embodiments are combined with one another, the advantages associated with the respective embodiments supplement one another correspondingly. It is pointed out at this early stage that, in spite of the additional presence of, for example, DMP, benzene and/or low boilers in the hydrocarbon mixture (HM1), the process according to the invention can be performed even in its basic form (i.e. with only steps a) and b)) without additional performance of a prior DMP removal, a hydrogenation and/or a low boiler removal. In this arrangement, the specific (additional) advantages associated with the specific process variants do not occur additionally.

In some embodiments of the present invention, the hydrocarbon mixture (HM1) used may also comprise high boilers, especially DMP. If DMP is removed prior to the actual cyclohexane preparation process, the exceptionally complex separation, especially distillation, of DMP out of the cyclohexane process product can be avoided, especially when the DMP is 2,4-dimethylpentane (2,4-DMP) and it is present in the starting mixture in a concentration of >100 ppm. This distinctly reduces the energy intensity and apparatus complexity in the preparation of pure or high-purity cyclohexane. This is because the separation of the DMP from cyclohexane, the actual process product, is technically quite demanding and complex, especially where the 2,4-dimethylpentane (2,4-DMP) isomer of DMP is concerned. The standard boiling point of 2,4-DMP at 80.52° C. is very similar to the standard boiling point of cyclohexane (80.78° C.), whereas the standard boiling points of the other DMP isomers have a greater separation from cyclohexane (2,3-DMP has, for example, a standard boiling point of 89.88° C.).

The process according to the invention, in this process variant, advantageously allows complete or virtually complete removal of the DMP present in (HM1) by virtue of the prior removal from (HM1). Particular preference is given to performing the process according to the invention in such a way that the DMP present in (HM1) is removed completely or virtually completely (down to 2% based on the amount of all DMP isomers present in the starting mixture) from (HM1) by prior DMP removal.

The process according to the invention can additionally be performed irrespective of whether or not cyclohexane is already present in the hydrocarbon mixture used. If cyclohexane itself is also present alongside DMP in the hydrocarbon mixtures used, this cyclohexane present in (HM1), in the process according to the invention, is removed, preferably together with DMP, via the bottom. The disadvantage of a reduction in the amount of cyclohexane product, which is associated with this arrangement, however, is more than compensated for by the above-described reduction in energy intensity and apparatus complexity.

In one embodiment of the present invention, however, this cyclohexane present in (HM1) can be recovered. In this embodiment, the cyclohexane discharged from the process together with the high boilers, especially with DMP, is removed again from DMP by distillation, preferably by an extractive or azeotropic distillation. The cyclohexane obtained, which is essentially free of DMP, can be fed back to the actual process product (cyclohexane which is prepared by the process according to the invention) or fed into the process according to the invention at another point. The advantage in the case of this process variant over a removal from a point further on in the process (downstream), i.e., for example, from the cyclohexane product stream, is considered to be that the DMP removal has to be conducted from a much smaller amount of cyclohexane, since DMP is removed only from the cyclohexane present in the hydrocarbon starting mixture and not also from the cyclohexane formed in the hydrogenation and/or isomerization, which is the actual process product. Accordingly, for this separate DMP/cyclohexane separation, smaller apparatuses and a smaller amount of energy are required.

In some embodiments of the present invention, in spite of the aromatics removal connected downstream of the steamcracking process, the hydrocarbon mixture (HM1) used may also still comprise aromatics, especially benzene. Owing to the hydrogenation of the aromatics performed in these embodiments, the isomerization in step a) can be performed advantageously, preferably in the presence of an acidic ionic liquid. The advantage is considered to be that the aromatics remaining in (HM1), especially benzene, removed completely or at least substantially by an upstream hydrogenation, can be converted to the corresponding saturated hydrocarbons. Accordingly, the deactivation which otherwise occurs in the catalysts, especially acidic ionic liquids, used for isomerization, especially for isomerization of MCP to cyclohexane, by aromatics, especially by benzene or other unsaturated compounds, is reduced or entirely avoided.

In addition, the hydrogenation of the aromatics present in (HM1), if they comprise benzene, has the advantage that the amount of product obtained is increased by the cyclohexane obtained in the hydrogenation of the benzene.

The removal of the remaining aromatics, especially of benzene, has the additional advantage that any distillative workup steps executed subsequently are facilitated because the formation of azeotropes of aromatics which otherwise occurs, for example benzene with saturated $C_6$-$C_7$-alkanes, is avoided.

In some embodiments of the present invention, the hydrocarbon mixture (HM1) used may also comprise low boilers. In principle, low boilers, especially isohexanes, can be removed at various points in the process. It is particularly advantageous, however, especially in the case of aromaticscontaining, especially benzene-containing, hydrocarbon mixtures (HM1), to perform the removal of low boilers after the hydrogenation and before the isomerization. This is because a removal of low boilers prior to the hydrogenation would have the disadvantage that the benzene present in the hydrocarbon mixture prior to the hydrogenation forms azeotropes with at least some of the low boilers to be removed and would therefore be removed at least partly together with the low boilers. This would reduce the amount of product by the amount of benzene removed together with the low boilers.

Removal of low boilers after the isomerization would in turn have the disadvantage that the low boilers dilute the hydrocarbons to be isomerized, especially MCP, and would thus lead to a reduction in the space-time yield in the isomerization. In addition, the removal of isohexanes prior to the isomerization is advantageous, since the driving force for the isomerization of n-hexane to isohexanes in the subsequent isomerization stage is thus increased. The isomerization of n-hexane to isohexanes in the isomerization stage is again significant because, owing to the position of the boiling points, n-hexane (standard boiling point 68.7° C.) is much more difficult to remove from MCP (standard boiling point 71.7° C.) than the isohexanes (standard boiling points 49.7 to 63.3° C.). Since, however, the isomerization stage is preferably followed by a distillative separation in which MCP is separated from the cyclohexane formed together with open-chain hexanes and is recycled upstream of or into the isomerization, which again necessitates the discharge of the open-chain hexanes from the process, it is advantageous owing to said position of the boiling points to discharge the open-chain hexanes from the process predominantly in the form of isohexanes, while an accumulation thereof, which is limited by the isomerization of n-hexane, can be accepted.

In the context of the present invention, a distillation can be performed in the embodiments known to those skilled in the art (see, for example, Kirk-Othmer Encyclopedia of Chemical Technology Published Online: 17 Aug. 2001, Vol. 8 p. 739 ff.). The respective distillation techniques are performed in the corresponding apparatuses known to those skilled in the art. The performance of an extractive distillation for separation of close-boiling substances is described, for example, in U.S. Pat. No. 4,053,369, U.S. Pat. No. 4,955,468 or WO 02/22528. Distillation using dividing wall columns is described, for example, in EP1127601 B1.

In the context of the present invention, a distillation is preferably configured as a rectification, meaning that the term "distillation column" is preferably understood to mean a rectifying column. The term "rectification", which is performed in a corresponding rectifying column (rectifying apparatus), also called rectification column or rectification apparatus, is understood to mean the following: in rectification, the vapor produced by distillation is conducted in countercurrent to a portion of the condensate thereof in a rectifying column. In this way, more volatile components are enriched in the top product and less volatile components in the bottom product of the rectifying column.

In the present context, the term "rectification column" also includes secondary apparatuses known in each case to the person skilled in the art, for example one or more reboilers, at least one condenser and optionally vessels and pumps. Accordingly, the withdrawal of streams from the rectification column is understood such that the respective stream is optionally passed through one or more of these secondary apparatuses, optionally also with a change in the state of matter and/or return of a portion of the stream withdrawn. For example, the withdrawal of a stream via the top of the rectification column should be understood such that the vapor stream obtained at the top of the column is at least partly condensed and subsequently divided into a return stream and a top product stream. The top product stream is then equivalent to the stream referred to in simplified form in the text which follows as "stream withdrawn via the top". Analogously, the specification of the feeding of a stream to a rectification column also includes the option that the stream in question, prior to entry into the column itself, passes through one or more secondary apparatuses, for example a preheater or pre-evaporator.

In the context of the present invention, the term "dimethylpentanes" (DMP) is understood to mean all known isomers of dimethylpentane, especially 2,2-dimethylpentane (2,2-DMP; standard boiling point: 79.17° C.), 2,3-dimethylpentane (2,3-DMP; standard boiling point: 89.88° C.), 3,3-dimethylpentane (3,3-DMP; standard boiling point: 86.09° C.) and 2,4-dimethylpentane (2,4-DMP; standard boiling point: 80.52° C.). This means that, in the embodiments of the process according to the invention relating to DMP-containing mixtures or streams, at least one dimethylpentane isomer is present in the corresponding mixtures or streams, preferably mixtures of two or more dimethylpentane isomers, one of these isomers preferably being 2,4-dimethylpentane.

In the context of the present invention, the term "compounds having a standard boiling point of 79 to 84° C." is understood to mean all hydrocarbons which, at standard pressure, boil within the range from 79 to 84° C. and which, individually or as a mixture, may at first be present in the hydrocarbon mixture (HM1) in the process according to the invention. In the process according to the invention, one single compound or several of these compounds may be separated from one another. One single compound or several of these compounds may also be referred to separately in the text which follows as a constituent of mixtures or streams. If this is the case, only the specific compounds listed in each case are an obligatory constituent of the corresponding mixture or stream; the other compounds having a standard boiling point of 79 to 84° C. which are not named in the corresponding stream or mixture may (unless stated otherwise or no longer possible, for example owing to a preceding removal) likewise be present in the corresponding stream or mixture. One single compound or several of these compounds may also be covered by the definition of another selection of compounds, for example by the definition of the term "$C_5$-$C_6$-alkanes".

Examples of compounds having a standard boiling point of 79 to 84° C. are cyclohexane (80.78° C.), 2,2-DMP (79.17° C.), 2,4-DMP (80.52° C.), 2,2,3-trimethylbutane (80.87° C.) and benzene (80.08° C.).

The same as stated above for the compounds having a standard boiling point of 79 to 84° C. also applies in the context of the present invention to compounds covered by the term "high boilers having a standard boiling point >84° C.". Examples of high boilers having a standard boiling point >84° C. are 3,3-DMP (86.09° C.), 2,3-DMP (89.88° C.), and the isoheptanes 2-methylhexane (2-MH; 90.06° C.), 3-methylhexane (3-MH; 91.87° C.) and 3-ethylpentane (3-EP; 93.45° C.).

In the context of the present invention, the two aforementioned groups of compounds (compounds having a standard boiling point of 79 to 84° C. and high boilers having a standard boiling point >84° C.) may also be combined to form one group of compounds. In this situation, the compounds are referred to correspondingly as "high boilers having a standard boiling point >78° C.". The above remarks regarding the two individual groups also apply analogously to this group of compounds. In the context of the present invention, the high boilers having a standard boiling point >78° C. are also referred to as "alkanes having 7 or more carbon atoms", i.e. the alkanes having 7 or more carbon atoms constitute a subgroup of the high boilers having a standard boiling point >78° C.

In addition, in the context of the present invention, the group of compounds having a standard boiling point >84° C. may also be included as a subgroup in the group which is referred to as "higher-boiling components than cyclohexane". The latter group thus additionally also includes compounds having a standard boiling point >80.78° C. up to and including 84° C.

In the context of the present invention, the term "majority" in connection with a stream (feed stream)—unless stated otherwise—means at least 50%, preferably at least 80%, more preferably at least 95%, especially at least 99% (the values should be understood as proportions of the respective feed stream).

Figure 6:
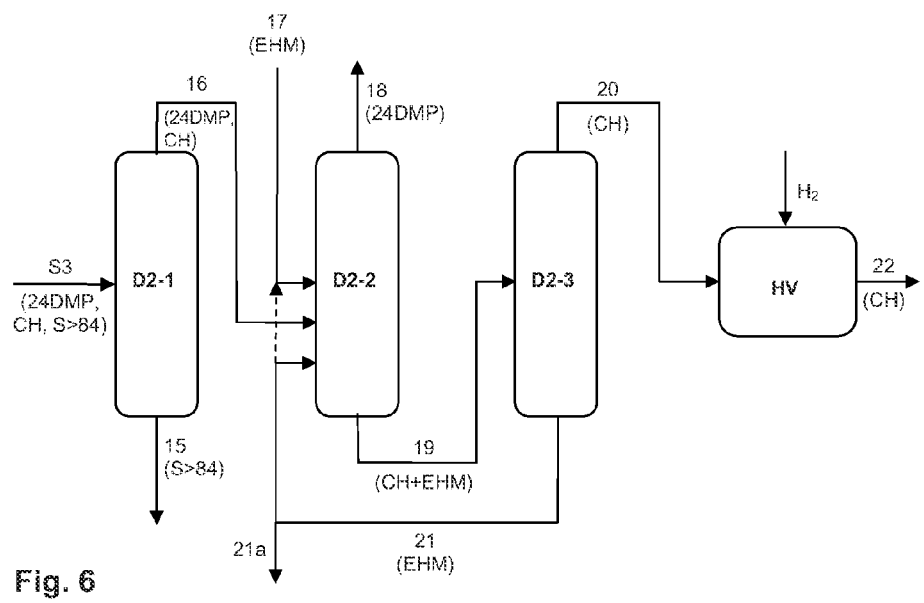
FIG. 6 shows an exemplary specific configuration for recovery of cyclohexane, where this is already present together with high boilers, especially with DMP, in the hydrocarbon mixture (HM1).
Figure 7:
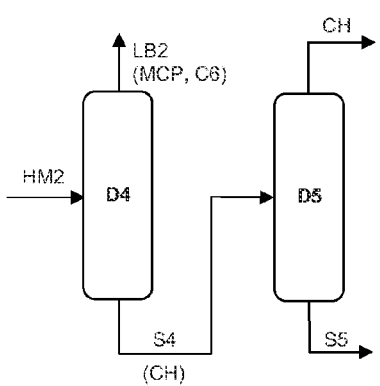
FIG. 7 shows an exemplary specific configuration of the isolation of cyclohexane in step b).

The process according to the invention for preparation of cyclohexane with starting materials originating from a steamcracking process is defined in detail hereinafter. In this context, reference is also made to FIGS. 1 to 7. FIG. 1 shows the process according to the invention in its basic form, including steps a) and b). FIGS. 2 to 5 illustrate specific configurations of the process according to the invention connected upstream of step a). FIG. 6 shows a specific configuration for recovery of cyclohexane, where this is already present together with high boilers, especially with DMP, in the hydrocarbon mixture (HM1). FIG. 7 relates to a specific configuration of the isolation of cyclohexane in step b). All figures are defined in detail at the appropriate point in the text which follows.

In the context of the present invention, in step a), a hydrocarbon mixture (HM1) comprising methylcyclopentane (MCP) is isomerized in the presence of a catalyst to obtain a hydrocarbon mixture (HM2) comprising cyclohexane, (HM1) being obtained in an apparatus for aromatics removal, preferably for benzene removal, connected downstream of a steamcracking process from a stream (S1) originating from the steamcracking process.

In principle, in the context of the present invention, it is possible to use any desired hydrocarbons as hydrocarbon mixture (HM1), provided that at least one of the hydrocarbons used is MCP which is subjected in step a) to an isomerization to cyclohexane in the presence of a catalyst, especially in the presence of an acidic ionic liquid. As well as MCP, further hydrocarbons present in (HM1) may optionally also be isomerized. On the basis of his or her specialist knowledge, the person skilled in the art knows which hydrocarbons are isomerizable by means of catalysts, especially by means of acidic ionic liquids.

In the context of the present invention, preference is given to using hydrocarbon mixtures (HM1) which, apart from MCP, comprise further components, for example hydrogenatable hydrocarbons. Optionally, such mixtures may also comprise compounds which are not themselves hydrocarbons but are miscible therewith.

The individual components of the hydrocarbon mixture (HM1) may be present in any desired concentrations/ratios relative to one another. The hydrocarbon mixture (HM1) preferably comprises at least 90% by weight, preferably at least 95% by weight, of hydrocarbons having 5 to 8 carbon atoms, provided that at least one of the hydrocarbons used is MCP. The hydrocarbons may otherwise be saturated or unsaturated and/or cyclic, linear or branched. More particularly, the hydrocarbon mixture (HM1) comprises between 10% by weight and 60% by weight, more preferably between 20% by weight and 50% by weight, of MCP and/or between 1% by weight and 30% by weight, more preferably between 4% by weight and 20% by weight, of benzene. If the hydrocarbon mixture (HM1) comprises an aromatic, especially benzene, in the above-specified ranges, in the process according to the invention, the isomerization is preferably preceded by performance of a hydrogenation, as described in detail below in the context of embodiment A.

In a preferred embodiment of the present invention, the hydrocarbon mixture (HM1) comprises benzene, methylcyclopentane (MCP) and at least one further compound selected from cyclohexane, cyclopentane, olefins and acyclic $C_5$-$C_8$-alkanes. In this embodiment, the further compounds preferably also comprise at least one low boiler selected from linear or branched $C_5$-alkanes, cyclopentane and linear or branched $C_6$-alkanes. The term "olefin" comprises, as well as linear, monounsaturated olefins such as pentene or hexene, also cyclic olefins, especially cyclohexene, and also dienes and cyclic dienes. In addition, the group of the $C_5$-$C_8$-alkanes may also include compounds having a standard boiling point >78° C., also called "high boilers" hereinafter. Such compositions of (HM1) are preferably used in connection with embodiments A, B, C and/or D described below, a hydrogenation preferably always being performed owing to the presence of benzene. The further purification steps according to embodiments A to D are performed only if the optional cyclohexane, high boiler and/or low boiler components are also present to a significant degree in these compositions.

More preferably, the hydrocarbon mixture (HM1) comprises benzene, methylcyclopentane (MCP) and at least one further hydrocarbon selected from cyclohexane, n-hexane, isohexanes, n-heptane, isoheptanes, methylcyclohexane or dimethylcyclopentanes.

In a further preferred embodiment of the present invention, the hydrocarbon mixture (HM1) additionally comprises cyclohexane. Such a composition of (HM1) is preferably used in connection with embodiments C and D described below. (HM1) preferably comprises
i) benzene,
ii) MCP,
iii) DMP,
iv) cyclohexane and
v) optionally at least one further compound selected from olefins and $C_5$-$C_8$-alkanes.

In component v) of the hydrocarbon mixture (HM1), the term "olefin" comprises, as well as linear, monounsaturated olefins such as pentene or hexene, also cyclic olefins, especially cyclohexene, and also dienes and cyclic dienes. In addition, the group of the $C_5$-$C_8$-alkanes also includes high boilers having a standard boiling point >78° C. The hydrocarbon mixture (HM1) may optionally also comprise hydrocarbons having more than eight carbon atoms and/or hydrocarbons having a relatively low boiling point, for example those having fewer than five carbon atoms.

In the context of the present invention, the hydrocarbon mixture (HM1) is obtained from an apparatus for aromatics removal. Apparatuses for aromatics removal as such are known to those skilled in the art; they may comprise, for example, one, two or more interconnected distillation apparatuses. The aromatics removal is preferably performed as an extractive aromatics distillation, especially as an extractive benzene distillation. A portion of the hydrocarbon mixture (HM1) and/or individual components present therein may originate from a source other than the apparatus for aromatics removal or else from a process other than the steamcracking process. For example, these portions and/or individual components can subsequently be added to the hydrocarbon mixture (HM1) obtained in the apparatus for aromatics removal.

The apparatus for aromatics removal in turn is connected downstream of a steamcracking process. A stream (S1) originating from the steamcracking process is introduced into the apparatus for aromatics removal. In the apparatus for aromatics removal, stream (S1) is separated into an aromatics-rich stream (S2) and the hydrocarbon mixture (HM1). This is illustrated once again in the text which follows in combination with FIG. 1.

The performance of a steamcracking process as such is known to those skilled in the art. The features of the steamcracking process have already been described in the introduction to the present invention, and reference is made thereto. In the context of the present invention, the steamcracking process preferably comprises a naphtha cracker (naphtha steamcracking process). Stream (S1) thus preferably originates from a naphtha cracker and/or stream (S1) comprises pyrolysis gasoline or a substream separated from the pyrolysis gasoline.

Stream (S1) is also referred to as the feed stream (S1) to the apparatus for aromatics removal. Stream (S1) comprises the hydrocarbon mixture (HM1) and additionally a proportion of aromatics. These additional aromatics are thus separated from the hydrocarbon mixture (HM1) in the apparatus for aromatics removal. This additionally means that the hydrocarbon mixture (HM1) has a lower concentration of aromatics, especially benzene, than the feed stream (S1) to the apparatus for aromatics removal; for example, the hydrocarbon mixture (HM1) may have a concentration of aromatics at least 50% lower than the feed stream (S1) to the apparatus for aromatics removal.

As already stated in the introduction in connection with the pyrolysis gasoline, the aromatics separation in the context of the present invention may also be preceded by a separation into fractions enriched in benzene, in toluene and in xylenes, optionally supplemented by further process steps. In this case, the benzene-enriched fraction is to be understood as stream (S1).

The benzene-enriched fraction is then preferably separated by means of extractive distillation, for example using N-formylmorpholine as an assistant, into a stream comprising benzene in high purity and a benzene-depleted stream, which is also referred to as C6 nonaromatic stream (C6-NA). In this case, the hydrocarbon mixture (HM1) according to the present invention can be equated with the C6 nonaromatic stream (C6-NA).

C6-NA may comprise:
- linear open-chain and/or branched and cyclic (naphthenic) C5 hydrocarbons, for example n-pentane, isopentanes, cyclopentane,
- linear open-chain and/or branched and cyclic (naphthenic) C6 hydrocarbons, for example n-hexane, isohexanes, methylcyclopentane (MCP), cyclohexane,
- linear open-chain and/or branched and cyclic (naphthenic) C7 hydrocarbons, for example n-heptane, isoheptanes, for example dimethylpentanes (DMP), methylcyclohexane (MCP), dimethylcyclopentanes,
- olefins and/or aromatics, the structure of which is derived from one or more of the aforementioned hydrocarbons by means of elimination of hydrogen, for example benzene or cyclohexene.

As already stated in the introduction, the aromatics removal may vary within wide limits as a function of the specific composition of the aromatics-rich stream originating from the steamcracking process. For example, it is possible that all aromatics including benzene have already been separated from the other hydrocarbons in the aromatics removal. In general, however, the aromatics removal is executed and operated such that the majority of the benzene present in stream (S1) is drawn off from the process together with other aromatics via stream (S2), but a portion of the benzene remains in the hydrocarbon mixture (HM1). The same also applies to other aromatics which may be present in the hydrocarbon mixture (HM1).

The isomerization of MCP to cyclohexane in step a) is effected in the presence of a catalyst. Suitable catalysts are in principle all catalysts known for this purpose to those skilled in the art, for example Friedel-Crafts catalysts according to U.S. Pat. No. 2,846,485 such as aluminum chloride which may additionally contain HCl, or metal halides according to U.S. Pat. No. 3,311,667 such as aluminum chloride, zirconium chloride or boron trifluoride. Additionally suitable as catalysts are also the zeolites used in EP-A 1 995 297, or ionic liquids as used, for example, in WO 2011/069929.

In the context of the present invention, the isomerization is preferably effected in the presence of an acidic ionic liquid having the composition $K1Al_nX_{(3n+1)}$ where K1 is a monovalent cation, X is halogen and $1<n<2.5$. For example, mixtures of two or more acidic ionic liquids may be used, preference being given to using one acidic ionic liquid.

K1 is preferably an unsubstituted or at least partly alkylated ammonium ion or a heterocyclic (monovalent) cation, especially a pyridinium ion, an imidazolium ion, a pyridazinium ion, a pyrazolium ion, an imidazolinium ion, a thiazolium ion, a triazolium ion, a pyrrolidinium ion, an imidazolidinium ion or a phosphonium ion. X is preferably chlorine or bromine.

The acidic ionic liquid more preferably comprises, as a cation, an at least partly alkylated ammonium ion or a heterocyclic cation and/or, as an anion, a chloroaluminate ion having the composition $Al_nCl_{(3n+1)}$ where $1<n<2.5$. The at least partly alkylated ammonium ion preferably comprises one, two or three alkyl radicals (each) having one to ten carbon atoms. If two or three alkyl substituents are present with the corresponding ammonium ions, the respective chain length can be selected independently; preferably, all alkyl substituents have the same chain length. Particular preference is given to trialkylated ammonium ions having a chain length of one to three carbon atoms. The heterocyclic cation is preferably an imidazolium ion or a pyridinium ion.

The acidic ionic liquid especially preferably comprises, as a cation, an at least partly alkylated ammonium ion and, as an anion, a chloroaluminate ion having the composition $Al_nCl_{(3n+1)}$ where $1<n<2.5$. Examples of such particularly preferred acidic ionic liquids are trimethylammonium chloroaluminate and triethylammonium chloroaluminate.

Furthermore, in the isomerization, in addition to the acidic ionic liquid, it is also possible to use a hydrogen halide (HX) as a cocatalyst. The hydrogen halides (HX) used may in principle be any conceivable hydrogen halides, for example hydrogen fluoride (HF), hydrogen chloride (HCl), hydrogen bromide (HBr) or hydrogen iodide (HI). The hydrogen halides can optionally also be used as a mixture, but preference is given in the context of the present invention to using only one hydrogen halide. Preference is given to using the hydrogen halide whose halide moiety is also present in the above-described acidic ionic liquid (at least partly) in the corresponding anion. The hydrogen halide (HX) is preferably hydrogen chloride (HCl) or hydrogen bromide (HBr). The hydrogen halide (HX) is more preferably hydrogen chloride (HCl).

The apparatus (IV) used for performance of the isomerization may in principle be any apparatuses known to the person skilled in the art for such a purpose. The apparatus (IV) is preferably a stirred tank or a stirred tank cascade. A "stirred tank cascade" means that two or more, for example three or four, stirred tanks are connected in succession (in series).

The isomerization is preferably performed at a temperature between 0° C. and 100° C., especially preferably at a temperature between 30° C. and 60° C. It is additionally preferable that the pressure in the isomerization is between 1 and 20 bar abs. (absolute), preferably between 2 and 10 bar abs.

The performance of the isomerization in step a), preferably of an isomerization of MCP in the presence of an acidic ionic liquid as a catalyst and optionally a hydrogen halide as a cocatalyst, is known to those skilled in the art. The hydrocarbons (i.e. MCP and any other hydrocarbons present in (HM1)) and the ionic liquid in the isomerization preferably each form a separate phase, though portions of the ionic liquid may be present in the hydrocarbon phase and portions of the hydrocarbons in the ionic liquid phase. If present, the hydrogen halide, especially hydrogen chloride, is introduced, preferably in gaseous form, into the apparatus (IV) for performance of the isomerization. The hydrogen halide may, at least in portions, be present in the two aforementioned liquid phases and in a gaseous phase which is preferably additionally present.

Preference is given to performing the isomerization in the apparatus (IV) in such a way that two liquid phases and one gas phase are present in a stirred tank or a stirred tank cascade. The first liquid phase comprises the acidic ionic liquid to an extent of at least 90% by weight and the second liquid phase comprises the hydrocarbons to an extent of at least 90% by weight. The gas phase comprises at least one hydrogen halide, preferably hydrogen chloride, to an extent of at least 90% by weight. Optionally, a solid phase may also be present, this comprising components from which the ionic liquid is formed in solid form, for example $AlCl_3$. The pressure and composition of the gas phase are set here such that the partial pressure of the gaseous hydrogen halide, especially of HCl gas, in the gas phase is between 0.5 and 20 bar abs. (absolute), preferably between 1 and 10 bar abs.

It is additionally preferable in the context of the present invention that the isomerization is performed in a dispersion (D1), with dispersion of phase (B) in phase (A) in the dispersion (D1), the volume ratio of phase (A) to phase (B) being in the range from 2.5 to 4:1 [vol/vol], phase (A) comprising >50% by weight of at least one acidic ionic liquid, and phase (B) comprising >50% by weight of at least one nonaromatic hydrocarbon. It is additionally preferable that the dispersion (D1) additionally comprises HCl and/or gaseous HCl is introduced into the dispersion (D1).

As already stated above, in the isomerization in the presence of a catalyst, preferably of an acidic ionic liquid, and optionally of a hydrogen halide (HX), MCP is at least partly isomerized to cyclohexane. Further hydrocarbons present in (HM1) apart from MCP may be isomerized. The hydrocarbons obtained in the isomerization are present in the hydrocarbon mixture (HM2). Mixture (HM2) thus differs in terms of composition and/or amount of the hydrocarbons present therein from the corresponding hydrocarbon mixture (HM1) present prior to the isomerization. The hydrocarbon mixture (HM1) has already been defined above.

Since the isomerization to be performed in such isomerization processes usually does not proceed to an extent of 100% (i.e. to completion), the product generally still also comprises the hydrocarbon with which the isomerization has been performed (in a smaller amount than before the isomerization). Since, in the present case, MCP is isomerized to cyclohexane, the isomerization product generally comprises a mixture of cyclohexane and (in a smaller amount than before the isomerization) MCP.

All components of the hydrocarbon mixture (HM1) which are not isomerized in step a), however, are likewise present in the hydrocarbon mixture (HM2). It should, though, be borne in mind that the isomerization in step a) may be preceded by the performance of additional intermediate steps with the hydrocarbon mixture (HM1) originating from the apparatus for aromatics removal. Such intermediate steps are described in the text which follows as embodiments A to C, for example. If one or more of these intermediate steps is performed, the isomerization (as detailed below) is effected using not (HM1) but, for example, with the hydrocarbon mixtures (HM1a) or (HM1b). If this is the case, it is necessary instead to relate the composition of (HM2) to the hydrocarbon mixtures (HM1a) or (HM1b).

In step b) of the process according to the invention, cyclohexane is isolated from the hydrocarbon mixture (HM2).

The cyclohexane can be isolated by methods known to those skilled in the art, for example using one or more distillation columns into which the output from the apparatus in which the isomerization in step a) has been performed is introduced. Preference is given to isolating the cyclohexane in step b) using at least one distillation column, especially using at least one rectification column. The columns/apparatuses (D4) to (D6) described hereinafter are thus preferably each configured as rectification columns. In general, in the process according to the invention, after the isomerization, cyclohexane is isolated in a purity of at least 98% by weight, preferably of at least 99.5% by weight, more preferably of at least 99.9% by weight.

Preference is given to performing step b) of the process according to the invention in such a way that the hydrocarbon mixture (HM2) comprising cyclohexane, MCP, possibly acyclic $C_5$-$C_6$-alkanes and possibly higher-boiling components than cyclohexane is fed into a distillation column (D4), and the majority of the MCP and, if present, of acyclic $C_5$-$C_6$-alkanes present in the feed to (D4) is removed from (D4) at a withdrawal point above the feed, preferably via the top. If acyclic $C_5$-$C_6$-alkanes are present in (HM2), these are preferably $C_6$-alkanes, more preferably n-hexane and isohexanes. This stream comprising the majority of MCP (and possibly of acyclic $C_5$-$C_6$-alkanes) is also referred to hereinafter as stream (LB2).

Stream (LB2) is further characterized in that it (relative to (HM2)) is enriched in MCP and depleted of cyclohexane, this stream (LB2) preferably comprising less than 20% by weight, preferably less than 10% by weight, more preferably less than 7% by weight, of cyclohexane. It is additionally preferable that stream (LB2) is recycled into or upstream of the apparatus for isomerization.

The expression "recycling upstream of the apparatus for isomerization" may, in accordance with the invention, mean that stream (LB2) can be recycled fully or partly, actually into or upstream of process steps, or the corresponding apparatuses for performance of these process steps, which are in turn themselves connected upstream of the isomerization. Such process steps are, for example, the low boiler removal according to embodiment B described hereinafter. Stream (LB2) can thus be recycled fully or partly into or upstream of the apparatus for performance of the low boiler removal.

The cyclohexane can be drawn off from the distillation column (D4), preferably if no higher-boiling components than cyclohexane are present in a concentration which impairs the respective specification, in a purity of at least 98% by weight, preferably of at least 99.5% by weight, more preferably of at least 99.9% by weight, via the bottom of (D4) or a side draw from (D4) below the feed, preferably a vaporous side draw from (D4) (option b0)).

Alternatively, it is also possible to implement option b1), wherein the cyclohexane-enriched stream drawn off via the bottom of (D4) is introduced into a distillation column (D5), and a stream (S5) comprising higher-boiling components than cyclohexane is removed via the bottom of (D5) and cyclohexane is drawn off with a purity of at least 98% by weight, preferably of at least 99.5% by weight, more preferably of at least 99.9% by weight, via a takeoff point above the feed to (D5), preferably via the top.

Alternatively, it is also possible to implement option b2), wherein a cyclohexane-enriched stream, which is preferably in vaporous form, is removed via the side draw from the distillation column (D4), the side draw preferably being in the stripping section of (D4) and/or the cyclohexane-enriched stream from the side draw of (D4) being passed into an apparatus (D6) for further purification, preferably in the form of a distillation column, and cyclohexane being obtained therein via a takeoff point above the feed to (D6), preferably via the top, with a purity of at least 98% by weight, preferably of at least 99.5% by weight, more preferably of at least 99.9% by weight.

In option b2), it is additionally preferable that the feed of the preferably vaporous stream from (D4) to (D6) is below the lowermost tray, the lowermost structured packing element or the lowermost random packing element of (D6), and (D6) is operated with a top condenser and partial reflux of the condensate drawn off therefrom, but not with a dedicated reboiler, and that the liquid obtained at the bottom in (D6) is passed back into the distillation column (D4) at about the level of the side draw. In this embodiment, a stream (S5) comprising higher-boiling components than cyclohexane is drawn off via the bottom of (D4).

Alternatively, it is also possible to implement option b3), wherein the distillation column (D4) takes the form of a dividing wall column, the dividing wall is partly below the feed point, a draw point is in the region of the dividing wall and this draw point is used to withdraw a preferably liquid cyclohexane stream having a purity of at least 98% by weight, preferably of at least 99.5% by weight, more preferably of at least 99.9% by weight. In this embodiment, a stream (S5) comprising higher-boiling components than cyclohexane is likewise drawn off via the bottom of (D4).

FIG. 7 once again illustrates step b) of the process according to the invention as per the above-described option b1). CH means cyclohexane, C6 means acyclic $C_5$-$C_6$-alkanes, especially isohexanes, and the bracketed expressions indicate the components most relevant to the process and/or the main components of the respective stream. In the embodiment according to FIG. 7, a hydrocarbon mixture (HM2) comprising cyclohexane, MCP, acyclic $C_5$-$C_6$-alkanes, especially n-hexane, and high boilers having a standard boiling point >84° C. is used. From the bottom of D4, a cyclohexane-enriched stream (S4) is introduced into the distillation column (D5), from which on-spec cyclohexane is isolated via the top. The bottom stream (S5) comprises higher-boiling components than cyclohexane.

In the context of the present invention, after the isomerization in step a) and prior to a distillative removal/isolation of the cyclohexane in step b), additional purification steps may be performed with the output from the isomerization. These purification steps may, for example, be a neutral and/or alkaline wash, which can be performed in one or more stages. Additionally or alternatively to the wash, it is also possible to use specific apparatuses, for example distillation or rectifying apparatuses, in order, for example, to separate hydrogen halide present from the hydrocarbons. Such apparatuses also comprise apparatuses for one-stage evaporation, especially for flash evaporation. Additionally or alternatively, in the case of use of acidic ionic liquid, it is also possible to connect phase separation units, preferably phase separators, upstream of the aforementioned specific apparatuses, especially in order to separate the acidic ionic liquid from the hydrocarbons.

In a particularly preferred embodiment, the isomerization is performed in the presence of acidic ionic liquid and the output from the isomerization is conducted into a phase separation unit, for example a phase separator, where a separation into a phase consisting to an extent of at least 90% by weight of acidic ionic liquid and a phase consisting to an extent of at least 90% by weight of hydrocarbons is carried out. The phase consisting to an extent of at least 90% by weight of acidic ionic liquid is at least partly recycled into the isomerization and the phase consisting to an extent of at least 90% by weight of hydrocarbons is, after volatile constituents, for example HCl, have optionally been withdrawn therefrom in a distillation or rectifying apparatus, conducted into a neutral and/or alkaline wash, where residues of the ionic liquid or constituents thereof, for example HCl or $AlCl_3$, are removed.

FIG. 1 illustrates the process according to the invention once again in its basic form, including steps a) and b). CH means cyclohexane, SC means steamcracking process or apparatuses in which such a process is performed, VA means apparatus for aromatics removal and IV means isomerization apparatus. The hydrocarbon mixture (HM1) comprises at least MCP. If (HM1) additionally comprises at least one aromatic, especially benzene, at least one high boiler, especially DMP, and/or at least one low boiler, especially isohexanes, rather than the basic form of the process according to the invention described in the present FIG. 1, preference is given to performing one of the preferred embodiments of the process according to the invention illustrated in FIGS. 2 to 6 below.

In the process according to FIG. 1, a stream (S1) comprising aromatics, preferably benzene, and additionally the components of the hydrocarbon mixture (HM1) is first obtained from an upstream steamcracking process. This stream (S1) is fed into an apparatus for aromatics removal (VA). (VA) is preferably operated as an extractive aromatics distillation, especially as an extractive benzene distillation. An aromatics-rich, preferably benzene-rich, stream (S2) and the hydrocarbon mixture (HM1) are removed from (VA).

In step a), the hydrocarbon mixture (HM1) is subjected to an isomerization to obtain the hydrocarbon mixture (HM2), with at least partial conversion of MCP to cyclohexane.

The hydrocarbon mixture (HM1) is isomerized in an isomerization apparatus (IV) suitable for this purpose. The catalyst used in the isomerization is preferably an acidic ionic liquid, particular preference being given to performing the isomerization in a stirred tank or a stirred tank cascade.

Subsequently, cyclohexane is isolated in step b) from the isomerization product, for example using one or more distillation columns, into which the output of the isomerization apparatus (IV) is introduced; cyclohexane is separated therein from unconverted MCP and any further components, and the MCP-enriched and cyclohexane-depleted substream is preferably recycled upstream of or into the isomerization apparatus (IV). Step b) is shown in FIG. 1 in simplified form by the distillation apparatus (D4). Preference is given to performing step b) as described above in connection with FIG. 7. Accordingly, FIG. 1 indicates the optional removal of higher-boiling components than cyclohexane via stream (S5) as a possible variant by means of the dotted arrow.

If (HM1) additionally comprises at least one aromatic, especially benzene, a preferred embodiment of the process according to the invention is employed (also referred to hereinafter as "embodiment A"), in which the process additionally comprises step c), which is performed prior to step a), comprising c) hydrogenating the hydrocarbon mixture (HM1) comprising at least MCP and at least one aromatic to obtain a hydrocarbon mixture (HM1a) having a reduced amount of at least one aromatic compared to (HM1), with use of (HM1a) rather than (HM1) in the subsequent steps.

In other words, this means that, in step c), the aromatics present in the hydrocarbon mixture (HM1) in this embodiment are hydrogenated to obtain the corresponding nonaromatic hydrocarbons, preferably the fully saturated hydrocarbons which arise with retention of all carbon-carbon bonds. If other unsaturated compounds are present in the hydrocarbon mixture (HM1), for example olefins such as cyclohexene, these are likewise hydrogenated in step c) of the present invention. Preferably, the aromatic present in the hydrocarbon mixture (HM1) is benzene and/or the hydrocarbon mixture (HM1a) comprises an increased amount of cyclohexane compared to (HM1).

The hydrogenation of the hydrocarbon mixture (HM1) in embodiment A is effected, in the context of the present invention, in an apparatus (V) suitable for this purpose, this apparatus preferably comprising at least one hydrogenation reactor (HR). In the apparatus (V), benzene is hydrogenated to cyclohexane, the hydrogenation preferably being effected using elemental hydrogen. It is additionally preferable that the hydrogenation is effected in the liquid phase.

The hydrogenation of at least one aromatic in step c), preferably of benzene to cyclohexane, is generally performed in the presence of a suitable catalyst. Suitable catalysts are in principle all catalysts known to those skilled in the art for this purpose, for example a metal catalyst on kieselguhr according to U.S. Pat. No. 3,311,667 or metallic catalysts according to EP A 1 995 297, wherein the metals used with preference are the elements of the platinum group, tin or cobalt and molybdenum.

Preference is given to performing the hydrogenation in the presence of a catalyst comprising, as an active metal (also referred to as metal component or active component), at least one element of groups 8 to 10 of the Periodic Table of the Elements (PTE), for example iron, cobalt, nickel or ruthenium (corresponds to transition group VIIIB of the CAS Version of the PTE), especially nickel or ruthenium. It is additionally preferable that the active metal is applied to a support material (support). Suitable supports are in principle all supports known to those skilled in the art, for example $SiO_2$-containing, zirconia-containing or alumina-containing supports. Particular preference is given to using a catalyst comprising nickel as an active metal on an alumina-containing support.

The hydrogenation as such is executed and operated in a manner known per se to those skilled in the art, preference being given to a combination of a main reactor operated in an optionally cooled circuit (recycling of a portion of the mixture flowing out of the reactor into the mixture flowing into the reactor, with optional positioning of the cooling unit upstream or downstream of said feed) and a downstream postreactor operated in straight pass, i.e. without recycling. In this case, the apparatus (V) thus comprises two hydrogenation reactors (HR).

The hydrogenation reactors (HR) are preferably designed as fixed bed reactors without internal cooling. In this case, the hydrogenation is preferably operated such that the temperature differential between entering and exiting mixture is monitored continuously and, when this value falls below a particular target value, the entrance temperature is raised. It is additionally preferable that the hydrogenation reactors are operated in trickle mode.

It is additionally preferable that the hydrogenation is followed downstream by an apparatus in which decompression is effected to a pressure below the pressure established in the postreactor. This affords a gas stream which comprises hydrogen dissolved beforehand in the hydrocarbon mixture and is in any case compressed and recycled into at least one of the hydrogenation reactors (HR).

The hydrogenation is preferably performed at a temperature between 50 and 200° C., more preferably between 100 and 180° C., and/or a pressure between 10 and 300 bar abs., more preferably between 30 and 200 bar abs.

It is additionally preferable in the process according to the invention that the overall conversion of the aromatics, especially of the benzene (and of any other unsaturated compounds present in the hydrocarbon mixture (HM1)), in the hydrogenation is at least 90%, more preferably 99%, and/or the residual content of the aromatics, especially of the benzene (and of any other unsaturated compounds present in the hydrocarbon mixture (HM1)), in the hydrocarbon mixture (HM1a) is 1% by weight, preferably at most 0.1% by weight, more preferably at most 0.01% by weight.

Owing to the hydrogenation, in step c) of the invention, the hydrocarbon mixture (HM1a) is obtained, the composition of which differs from the hydrocarbon mixture (HM1) primarily with respect to the hydrogenated compounds. The hydrocarbon mixture (HM1a) thus comprises at least one hydrocarbon formed by hydrogenation of an aromatic and at least MCP which had already been present in (HM1). In addition, the hydrocarbon mixture (HM1a) comprises all other components as per hydrocarbon mixture (HM1) which are not chemically altered in the hydrogenation, and any hydrocarbons formed by hydrogenation of olefins or dienes. If the aromatic present in the hydrocarbon mixture (HM1) is benzene, the hydrocarbon mixture (HM1a) correspondingly comprises cyclohexane. If the hydrogenation in embodiment A is preceded by performance of a high boiler removal in embodiment C (see the corresponding text passages), the hydrogenation is performed using, rather than the hydrocarbon mixture (HM1), the corresponding hydrocarbon mixture (HM1b).

The hydrocarbon mixture (HM1a) preferably comprises cyclohexane, MCP, not more than 0.1% by weight of aromatics and possibly at least one further compound selected from olefins and acyclic $C_5$-$C_8$-alkanes. More preferably, the hydrocarbon mixture (HM1a) comprises cyclohexane, methylcyclopentane (MCP) and at least one further hydrocarbon selected from cyclohexane, n-hexane, isohexanes, n-heptane, isoheptanes, methylcyclohexane or dimethylcyclopentanes.

Particular preference is given to performing embodiment A in such a way that the aromatic present in the hydrocarbon mixture (HM1) is benzene and/or the hydrocarbon mixture (HM1a) comprises an increased amount of cyclohexane compared to (HM1).

Figure 2:
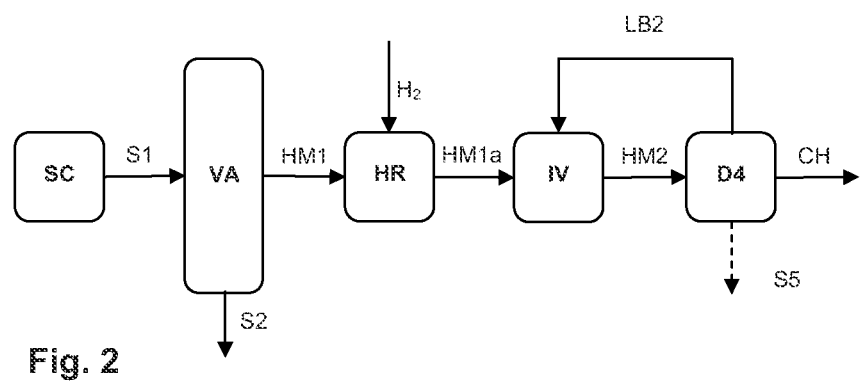
FIGS. 2 to 5 show exemplary specific configurations of the process according to the invention connected upstream of step a).

The above-described preferred embodiment A of the present invention including a hydrogenation is additionally illustrated in a preferred configuration in conjunction with FIG. 2. In FIG. 2, the abbreviations, arrows and other symbols have similar meanings to those explained above for FIG. 1. The hydrogenation is preferably performed in at least one reactor (HR), the hydrocarbon mixture (HM1) preferably comprising benzene, which is hydrogenated to cyclohexane.

In a further preferred embodiment of the process according to the invention (also referred to hereinafter as "embodiment B"), step a) is preceded by separation of at least one compound selected from linear or branched $C_5$-alkanes, cyclopentane and linear or branched $C_6$-alkanes from the hydrocarbon mixture (HM1). This separation, which is preferably performed by distillation, is also referred to hereinafter as "low boiler removal", which can be performed in the apparatuses known to those skilled in the art, especially using a distillation column (D3). Low boilers are understood to mean especially $C_5$-$C_6$-alkanes such as cyclopentane or isohexanes.

The hydrocarbon mixture (HM1) depleted of the low boilers is subsequently sent to the isomerization in step a) of the present invention. The hydrocarbon mixture (HM1) depleted of the low boilers is removed via a takeoff point below the feed, preferably from the bottom of the corresponding distillation column.

Preference is given to performing the low boiler removal in such a way that the isomerization in step a) is preceded by distillative separation of a stream (LB1) comprising at least one compound selected from linear or branched $C_5$-alkanes, cyclopentane or linear or branched $C_6$-alkanes, more preferably isohexanes, from the hydrocarbon mixture (HM1). Stream (LB1) is preferably drawn off via a takeoff point above the feed, more preferably via the top of the distillation column.

Preference is also given to an embodiment in which the stream (LB2) originating from step b) according to the description given above is recycled fully or partly into or upstream of (D3).

If the low boiler removal is preceded by performance of a hydrogenation in embodiment A and/or a high boiler removal in embodiment C (see the corresponding text passages), the low boiler removal is performed using, rather than the hydrocarbon mixture (HM1), the corresponding hydrocarbon mixtures (HM1a) and (HM1b).

Figure 3:
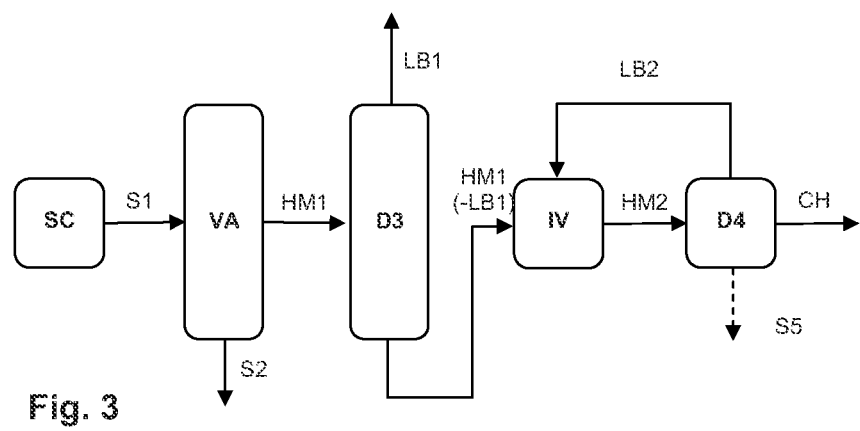

The above-described preferred embodiment B of the present invention including a low boiler removal is additionally illustrated below in a preferred configuration in conjunction with FIG. 3. In FIG. 3, the abbreviations, arrows and other symbols have similar meanings to those explained above for FIGS. 1 and 2.

In the distillation column (D3), the low boilers are removed from the hydrocarbon mixture (HM1) as stream (LB1), stream (LB1) boiling at a lower temperature than (HM1). Stream (LB1), compared to (HM1), is preferably enriched in isohexanes and/or cyclopentane and depleted of MCP. The hydrocarbon mixture (HM1) depleted of/reduced by stream (LB1), which is referred to in FIG. 3 as "HM1-(LB1)", boils at a higher temperature than (HM1). Stream (HM1-(LB1)) is preferably depleted of isohexanes and/or cyclopentane and enriched in MCP compared to (HM1).

The low boiler removal is preferably executed and operated in such a way that stream (LB1) comprises less than 5% by weight, more preferably less than 2.5% by weight, of MCP and stream (HM1-(LB1)) comprises less than 10% by weight, more preferably less than 5% by weight, of isohexanes.

Stream (LB1) can, for example, be introduced into a steamcracker as what is called cracker cofeed, while stream (HM1-(LB1)) is conducted into the isomerization stage. Optionally, within the low boiler removal, it is possible to draw off a further stream depleted of isohexanes and enriched in components having a lower boiling point than the isohexanes, for example chlorinated paraffins having <4 carbon atoms per molecule, compared to stream (LB).

In a further preferred embodiment of the process according to the invention (also referred to hereinafter as "embodiment C"), the process additionally comprises step d), which is performed prior to step a) and optionally prior to step c), comprising d) feeding the hydrocarbon mixture (HM1) into a distillation apparatus (D1),
(HM1) comprising at least methylcyclopentane, at least one alkane having 7 or more carbon atoms and possibly an aromatic,
at least one alkane having 7 or more carbon atoms being removed in (D1) from (HM1) to obtain the hydrocarbon mixture (HM1b), and
(HM1b) comprising a reduced amount of at least one alkane having 7 or more carbon atoms compared to (HM1), and (HM1b) being used rather than (HM1) in the subsequent steps.

Preferably, in the distillation apparatus (D1), the alkane having 7 or more carbon atoms (high boilers), especially DMP, present in the hydrocarbon mixture (HM1) is removed completely or virtually completely (down to 2% based on the amount of high boilers present in (HM1)) from (HM1), more particularly from the nonaromatic hydrocarbon and, if present, from the aromatic (i.e. the main components of the mixture (HM1b)). The alkane having 7 or more carbon atoms is drawn off from the distillation apparatus (D1) as stream (S3), which is preferably present in the bottom of (D1).

Alternatively, virtually complete high boiler removal, preferably virtually complete DMP removal, from the hydrocarbon mixture (HM1) can also be defined by the amount of high boilers, preferably of DMP, remaining in the mixture (HM1b) in relation to MCP and/or benzene. Taking this approach, it is especially preferable that the amount of high boilers, preferably of DMP, drawn off via the top in the distillation apparatus (D1) as mixture (HM1b), based on the sum of the amounts of MCP and benzene drawn off via the top, is at most 0.1% by weight, preferably at most 0.02% by weight.

The distillation apparatus (D1) is preferably a rectification column. It is additionally preferable that the outlet of the distillation apparatus (D1) from which the mixture (HM1b) is removed is above the feed with which the hydrocarbon mixture (HM1) is fed into (D1), the outlet preferably being in the top of (D1).

Figure 4:
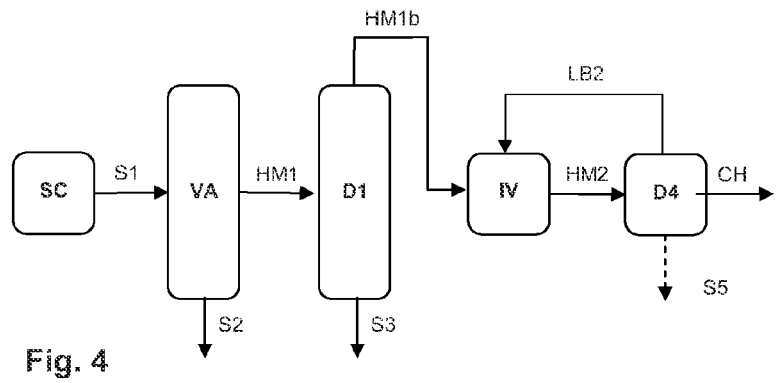

The above-described preferred embodiment C of the present invention including a high boiler removal is additionally illustrated in a preferred configuration in conjunction with FIG. 4. In FIG. 4, the abbreviations, arrows and other symbols have similar meanings to those explained above for FIGS. 1 to 3. The high boiler removal is performed in a distillation apparatus (D1), which is preferably a rectification column. The hydrocarbon mixture (HM1) preferably comprises MCP, DMP and possibly benzene. The high boilers, especially DMP, are preferably removed (virtually) completely from (D1) via stream (S3). If (HM1) also comprises an aromatic, preferably benzene, the hydrocarbon mixture (HM1b), after the high boiler removal, is preferably subjected to a hydrogenation, as illustrated hereinafter in combination with FIG. 5.

It is additionally preferable in embodiment C that step d) has the following component steps:
d1) feeding the hydrocarbon mixture (HM1) comprising
i) benzene,
ii) MCP,
iii) dimethylpentanes (DMP),
iv) cyclohexane and
v) optionally at least one further compound selected from olefins and $C_5$-$C_8$-alkanes
into the distillation apparatus (D1),
d2) removing a stream (S3) comprising DMP from an outlet of the distillation apparatus (D1), the outlet being below the feed, preferably at the bottom of (D1),
d3) removing the hydrocarbon mixture (HM1b) comprising benzene and/or MCP from an outlet of the distillation apparatus (D1), the outlet being above the feed, preferably at the top of (D1).

In this context, it is preferable that the hydrocarbon mixture (HM1b) comprises at least 95%, preferably at least 98%, of the portion consisting of benzene and MCP present in the hydrocarbon mixture (HM1), and/or that the hydrocarbon mixture (HM1b) comprises at most 0.1% by weight, preferably at most 0.02% by weight (based on the total amount of benzene and MCP in (HM1b)), of DMP, the hydrocarbon mixture (HM1b) more preferably comprising at most 0.015% by weight (based on the total amount of benzene and MCP in (HM1b)) of 2,4-DMP.

Stream (S3) removed from the bottom of the distillation apparatus (D1) comprises DMP and possibly further components. The further components are preferably cyclohexane, high boilers having a standard boiling point >78° C. and/or unsaturated compounds. Some of the unsaturated compounds can also be regarded as high boilers having a standard boiling point >78° C. The unsaturated compounds are preferably selected from benzene, olefins, cyclic olefins, especially cyclohexene, dienes and cyclic dienes. However, in the case of benzene, it is predominantly drawn off with stream (HM1a) owing to azeotrope formation with some of the components present in stream (HM1a).

Stream (S3) preferably comprises at least 98% of the DMP present in hydrocarbon mixture (HM1), more preferably at least 99% of the DMP. It is additionally preferable that stream (S3) removed from the bottom of the distillation apparatus (D1) comprises at most 10%, preferably at most 5%, more preferably at most 2%, of the MCP present in (HM1).

Figure 5:
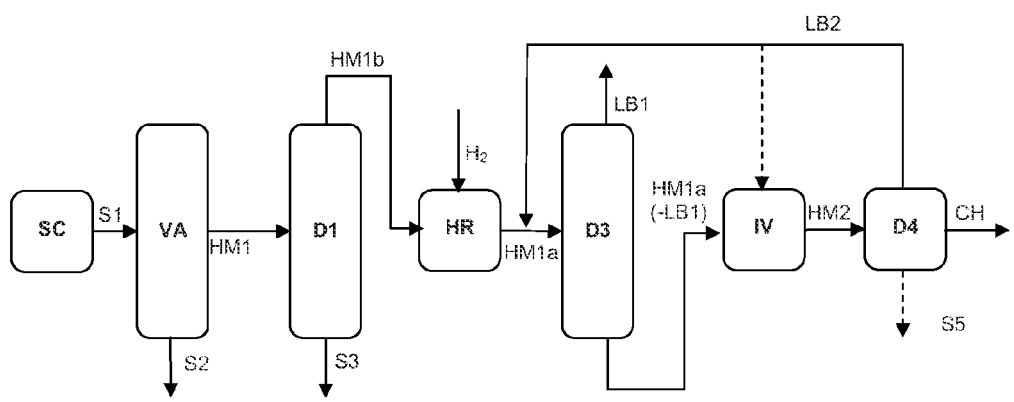

The above-described preferred embodiment C of the present invention including a high boiler removal in the presence of at least one aromatic, preferably benzene, is additionally illustrated in a preferred configuration in conjunction with FIG. 5. In FIG. 5, the abbreviations, arrows and other symbols have similar meanings to those explained above for FIGS. 1 to 4. The high boiler removal is performed in a distillation apparatus (D1), which is preferably a rectification column. The hydrocarbon mixture (HM1) preferably comprises MCP, DMP, benzene and possibly low boilers. The high boilers, especially DMP, are preferably removed (virtually) completely from (D1) via stream (S3). The hydrocarbon mixture (HM1b), after the high boiler removal, is subjected to a hydrogenation, as explained above in combination with FIG. 2. The low boiler removal in the distillation column (D3) which is executed after the hydrogenation in FIG. 5 is performed only when (HM1) comprises low boilers to a significant degree.

In a further preferred embodiment of the process according to the invention (also referred to hereinafter as "embodiment D"), stream (S3) is introduced into a distillation apparatus (D2), cyclohexane being separated from DMP in (D2). Embodiment D is a specific configuration of the above-described embodiment C which can be performed if the high boiler removal in embodiment C removes DMP and cyclohexane from the hydrocarbon mixture (HM1) used, or these two compounds are initially present in (HM1).

In this embodiment, D, of the process according to the invention, the cyclohexane present in stream (S3) is separated from the high boilers, especially from DMP, more particularly by distillation in a distillation apparatus (D2). This involves introducing stream (S3) into the distillation apparatus (D2), with separation of cyclohexane from DMP in (D2). The specific composition of stream (S3) has already been described above in connection with step d) of the invention.

The distillation or the distillation apparatus (D2) may have one or more stages, for example two or three stages; it preferably has three stages. In this context, the number of stages is understood to mean the number of columns, in each case including secondary apparatuses, for example reboilers and condensers, which together form the distillation apparatus (D2). A three-stage distillation apparatus (D2) thus means that a total of three columns, in each case including secondary apparatuses, for example reboilers and condensers, in each of which a distillation process can be performed, together form the distillation apparatus (D2). Preferably, (D2) comprises an extractive distillation column. It is additionally preferable that the cyclohexane-enriched stream drawn off from (D2) comprises at most 0.1% by weight, preferably at most 0.02% by weight, of DMP, more preferably at most 0.015% by weight of 2,4-DMP.

If the distillation apparatus (D2) comprises an extractive distillation column, the extractive distillation is preferably effected using an extraction aid (extraction assistant). The extraction aids used are generally compounds for which the following formula (I) applies:

$$\gamma_{DMP,E}^{\infty}/\gamma_{CH,E}^{\infty} > n \quad (1)$$

where
$\gamma_{DMP,E}^{\infty}$=activity coefficient of 2,4-dimethylpentane in the extraction aid at infinite dilution,
$\gamma_{CH,E}^{\infty}$=activity coefficient of cyclohexane in the extraction aid at infinite dilution,
n=preferably 1.1, more preferably 1.3.

The extraction aids used are preferably oxygen-containing open-chain or cyclic organic compounds having a boiling point at least 5 K above that of cyclohexane (81° C.), especially those comprising an amide function R—CO—NR'R" as a structural element, where R, R' and R" are (each independently) preferably selected from $C_1$-$C_{30}$-alkyl and H. Particularly suitable extraction aids are N-methylpyrrolidone and N-formylmorpholine. However, other compounds are also suitable, such as sulfolane, dimethyl sulfoxide or other compounds known to those skilled in the art as aprotic polar solvents. Also suitable are mixtures of a plurality of the compounds mentioned with one another or with water.

The cyclohexane/DMP separation preferably comprises the following steps i) to iii) and optionally step iv), the distillation apparatus (D2) being formed by the three components (D2-1) to (D2-3):
i) a rectifying column (D2-1) in which the majority of the high boilers having a standard boiling point >84° C. (based on the amount in the feed to (D2-1)) is removed via the bottom and the majority of the cyclohexane and other compounds having a standard boiling point of 79 to 84° C. (based on the amount in the feed to D2-1) is removed via the top, ii) an extractive distillation column (D2-2) in which the top product from (D2-1) is combined with an extraction aid and distilled in such a way that the majority of the extraction aid and of the cyclohexane is drawn off via the bottom and the majority of the other compounds having a standard boiling point of 79 to 84° C. present in the top product from (D2-1) is drawn off from (D2-2) via the top, iii) a regeneration column (D2-3) in which the majority of the cyclohexane present in the bottom stream from (D2-2) is drawn off via the top and the majority of the extraction aid present in the bottom stream from (D2-2) is drawn off via the bottom, and iv) optionally a hydrogenation apparatus into which either stream (S3) or the top product from (D2-3) is conducted.

In the context of the above steps i) to iv), the phrase "via the bottom" means a takeoff point below the feed, preferably the bottom, and the phrase "via the top" a takeoff point above the feed, preferably the top of the respective column.

The optional step iv) included in the above embodiment is generally performed only when stream (S3) comprises unsaturated compounds which are thus also fed into the distillation apparatus (D2) and which are additionally not discharged from the process via the bottom of the rectifying column (D2-1). The hydrogenation in the optional step iv) can be performed analogously to the hydrogenation in the above-described embodiment A, preferably in one stage. The hydrogenation apparatus may optionally also be connected upstream of the distillation apparatus (D2). In this case, stream (S3) is first conducted into the hydrogenation apparatus, then the hydrogenated stream (S3) is introduced into the distillation apparatus (D2), especially into the rectifying column (D2-1). This is an advantageous variant when stream (S3) comprises components, for example unsaturated hydrocarbons, which form azeotropes with the components to be drawn via the bottom of (D2-1).

The above-described preferred embodiment of the cyclohexane/DMP separation can optionally also be performed without a rectifying column (D2-1) as an obligatory constituent. In this variant, the cyclohexane/DMP separation is effected analogously using only the two columns (D2-2) and (D2-3), in which case there may optionally also be a downstream hydrogenation apparatus. This variant is preferably performed when stream (S3) comprises only a small proportion of, if any, high boilers having a standard boiling point >84° C.

The above-described preferred embodiment using the extractive distillation column (D2-2) is preferably executed and operated in such a way that the DMP-containing stream drawn off via the top from (D2-2) comprises less than 50% by weight, preferably less than 10% by weight, of cyclohexane. In addition, the cyclohexane-containing stream drawn off via the top of regeneration column (D2-3) comprises preferably less than 1% by weight, more preferably less than 10 ppm by weight, of extraction aid and/or less than 1% by weight, preferably less than 300 ppm by weight, of dimethylpentanes, more preferably less than 150 ppm by weight of 2,4-dimethylpentane.

It is additionally preferable that cyclohexane is isolated in a purity of 98% by weight, especially at least 99.5% by weight, from (D2). With regard to the performance of the isolation of the cyclohexane, the same considerations apply as detailed above in connection with the isolation of the cyclohexane in step b), especially in connection with the distillation apparatus (D4). Alternatively, the cyclohexane which originates from the distillation apparatus (D2) in embodiment D can be combined with the cyclohexane which has been prepared in the isomerization in step a) and/or possibly in the hydrogenation in step c).

The above-described embodiment D of the present invention is additionally illustrated in a preferred configuration in conjunction with FIG. 6. In FIG. 6, the abbreviations, arrows and other symbols have analogous meanings to those explained above for FIG. 1 or in the description of this preferred embodiment. In the embodiment according to FIG. 6, a distillation apparatus (D2) consisting essentially of three columns ((D2-1) to D2-3)) and connected upstream of a hydrogenation apparatus is used. The individual columns may additionally also comprise secondary apparatuses, such as reboilers or condensers, which are not shown in FIG. 6 for the sake of clarity. HV means hydrogenation apparatus, EHM means extraction aid, S>84 means high boilers having a standard boiling point >84° C., 24DMP means 2,4-dimethylpentane and the bracketed expressions indicate the components most relevant to the process and/or the main components of the respective stream. 24DMP is mentioned by way of example as a preferred component of the (other) compounds having a standard boiling point of 79 to 84° C. The extraction aid used is preferably N-methyl-2-pyrrolidone (NMP).

Stream (S3) which originates with preference from the bottom of the distillation apparatus (D1) and comprises DMP, cyclohexane, possibly unsaturated compounds and possibly high boilers having a standard boiling point >84° C., optionally after hydrogenation, is fed into the rectifying column (D2-1). The unsaturated compounds are preferably selected from benzene, olefins, cyclic olefins, especially cyclohexene, dienes and cyclic dienes. In (D2-1), the cyclohexane present in stream (S1) is concentrated, by first separating stream (S3) by means of rectification into a stream 15 enriched in higher-boiling components than cyclohexane (i.e., for example, 3,3-DMP and other high boilers having a standard boiling point >84° C. or unsaturated compounds having corresponding boiling points) and a stream 16 depleted of higher-boiling components than cyclohexane (stream 16 thus comprises cyclohexane and a majority of the other compounds having a boiling point of 79 to 84° C., at least a portion of the unsaturated compounds and a residual amount of high boilers having a standard boiling point >84° C.). Stream 15 can, for example, be conducted as a cofeed to a steamcracking process or be used as a constituent of fuel mixtures.

Stream 16 is conducted into an extractive distillation column (D2-2). At a point above the feed of stream 16, a stream 17 comprising at least one extraction aid (EHM) is conducted into the extractive distillation column (D2-2). At a point likewise above the feed of stream 16, preferably above the feed of stream 17, for example at the top of the column or downstream of the top condenser of the column, a stream 18 enriched in DMP, especially in 2,4-DMP, compared to stream 16 is withdrawn. Stream 18 preferably comprises a majority of the other compounds having a standard boiling point of 79 to 84° C., especially of 2,4-DMP, present in stream 16. Via a point below the feed of stream 16, preferably via the column bottom, a stream 19 comprising the extraction aid, cyclohexane and the unsaturated compounds is withdrawn, the cyclohexane/DMP concentration ratio, especially that of cyclohexane/2,4-DMP, being higher in stream 19 than in stream 16.

The extractive distillation column (D2-2) is preferably executed and operated in such a way that stream 18 comprises at most 100 ppm by weight, preferably at most 10 ppm by weight, more preferably at most 1 ppm by weight, of extraction aid. This can be achieved by virtue of the highest feed of an EHM-containing stream being at least 5, preferably at least 10, theoretical plates (as per the definition known to those skilled in the art) below the takeoff point of stream 18 and/or (D2-2) being operated with a reflux ratio of at least 5, preferably at least 10.

Stream 19, optionally after preheating, is conducted into the regeneration column (D2-3). From the regeneration column (D2-3), a stream 20 enriched in cyclohexane compared to stream 19 and a stream 21 depleted of cyclohexane compared to stream 19 (stream 21 comprises primarily the extraction aid, a portion of cyclohexane and any residual amount of other compounds having a standard boiling point of 79 to 84° C., especially of 2,4-DMP) are drawn off. From stream 21, a discharge stream (purge stream) 21a is branched off, this making up preferably not more than 5%, more preferably not more than 1%, of the amount of stream 21. The remaining stream, optionally after cooling (which can also be effected in a thermally integrated system with a preheating of stream 19), is supplied at least partly to stream 17 and/or recycled into the extractive distillation column (D2-2) in the vicinity of stream 16.

Stream 20 is optionally, together with a hydrogen-comprising stream, conducted into the hydrogenation apparatus (HV) in which, with the aid of a suitable catalyst, the unsaturated compounds selected from benzene, olefins, cyclic olefins, especially cyclohexene, dienes and cyclic dienes, are hydrogenated. Hydrogen can also be introduced into (HV) separately from stream 20, as shown in FIG. 6. Stream 22 obtained in the hydrogenation comprises cyclohexane as the main constituent and can optionally be worked up further; for example, on-spec (high-purity) cyclohexane can be isolated from stream 22. Stream 22 can optionally also be combined with the cyclohexane or a cyclohexane-containing stream which is prepared in the process according to the invention in apparatus (HR) and/or apparatus (IV) (in the basic form and/or embodiments A to C).

If the hydrocarbon mixture (HM1) also comprises an aromatic, it is preferably benzene. In the context of the present invention, preference is additionally given to performing a combination of the above-described embodiments A to C, as shown by way of example in FIG. 5, preferably in combination with the preferred embodiments in step b), as shown by way of example in FIGS. 7 and 8. In addition, preference is given to an additional combination with embodiment D.

The invention claimed is:

1. A process for preparing cyclohexane, comprising the following steps:
    a) isomerizing a hydrocarbon mixture (HM1) comprising methylcyclopentane (MCP) in the presence of an isomerization catalyst to obtain a hydrocarbon mixture (HM2) comprising cyclohexane, wherein the catalyst is an acidic ionic liquid,
        (HM1) being obtained from an apparatus for aromatics removal connected downstream of a steamcracking process, wherein a feed containing an aromatic entering the apparatus for aromatics removal comprises a stream (S1) originating from the steamcracking process, and
    b) isolating cyclohexane from the hydrocarbon mixture (HM2); wherein the process comprises step a-1), which is performed prior to step a), comprising
    a-1) hydrogenating the hydrocarbon mixture (HM1) comprising methylcyclopentane (MCP) and at least one aromatic to obtain a hydrocarbon mixture (HM1a) having methylcyclopentane (MCP) and a reduced amount of the at least one aromatic compared to (HM1), with use of (HM1a) rather than (HM1) in the subsequent steps a) and b).

2. The process according to claim 1, wherein the apparatus for aromatics removal is an extractive aromatics distillation, or the hydrocarbon mixture (HM1) has a lower concentration of aromatics than the feed stream (S1) to the apparatus for aromatics removal.

3. The process according to claim 1, wherein the aromatic present in the hydrocarbon mixture (HM1) is benzene or the hydrocarbon mixture (HM1a) comprises an increased amount of cyclohexane compared to (HM1).

4. The process according to claim 1, wherein the hydrogenation of the hydrocarbon mixture (HM1) is performed in the presence of a hydrogenation catalyst comprising, as an active metal, at least one element of groups 8 to 10 of the Periodic Table of the Elements.

5. The process according to claim 4, wherein the hydrogenation catalyst comprises nickel or ruthenium.

6. The process according to claim 1, wherein the hydrocarbon mixture (HM1) comprises benzene, methylcyclopentane (MCP) and at least one further compound selected from cyclohexane, cyclopentane, olefins and acyclic C5-C8-alkanes.

7. The process according to claim 1, wherein step a) is preceded by distillative separation of at least one compound selected from linear or branched C5-alkanes, cyclopentane and linear or branched C6-alkanes from the hydrocarbon mixture (HM1).

8. The process according to claim 1, additionally comprising step a-2), which is performed prior to step a) comprising
    a-2) feeding the hydrocarbon mixture (HM1) into a distillation apparatus (D1), (HM1) comprising methylcyclopentane (MCP), at least one alkane having 7 or more carbon atoms and optionally an aromatic, the at least one alkane having 7 or more carbon atoms being removed in (D1) from (HM1) to obtain a hydrocarbon mixture (HM1b)
        comprising methylcyclopentane (MCP) and a reduced amount of at the least one alkane having 7 or more carbon atoms compared to (HM1), and (HM1b) being used rather than (HM1) in the subsequent steps a) and b).

9. The process according to claim 8, wherein the step a-2) has the following component steps:
    d1) feeding the hydrocarbon mixture (HM1) comprising
        i) benzene,
        ii) MCP,
        iii) dimethylpentanes (DMP),
        iv) cyclohexane and
        v) optionally at least one further compound selected from olefins and $C_5$-$C_8$-alkanes into the distillation apparatus (D1),
    d2) removing a stream (S3) comprising DMP from an outlet of the distillation apparatus (D1), the outlet being at the bottom of (D1),
    d3) removing the hydrocarbon mixture (HM1b) comprising benzene or MCP from an outlet of the distillation apparatus (D1), the outlet being at the top of (D1).

10. The process according to claim 9, wherein the hydrocarbon mixture (HM1b) comprises at least 95% of the portion consisting of benzene and MCP present in the hydrocarbon mixture (HM1), or the hydrocarbon mixture (HM1b) comprises at most 0.1% by weight (based on the total amount of benzene and MCP in (HM1b)), of DMP.

11. The process according to claim 10, wherein the hydrocarbon mixture (HM1b) comprises at most 0.015% by weight (based on the total amount of benzene and MCP in (HM1b)) of 2,4-DMP.

12. The process according to claim 9, wherein the stream (S3) is introduced into a distillation apparatus (D2), cyclohexane being separated from DMP in (D2), and (D2) comprising an extractive distillation column or the cyclohexane-enriched stream drawn off from (D2) comprising at most 0.1% by weight of 2,4-DMP.

13. The process according to claim 12, wherein the cyclohexane/DMP separation comprises the following steps i) to iii) and optionally step iv), the distillation apparatus (D2) being formed by the three components (D2-1) to (D2-3):
  i) a rectifying column (D2-1) in which the majority of the high boilers having a standard boiling point >84° C. (based on the amount in the feed to (D2-1)) is removed via the bottom and the majority of the cyclohexane and other compounds having a standard boiling point of 79 to 84° C. (based on the amount in the feed to D2-1) is removed via the top,
  ii) an extractive distillation column (D2-2) in which the top product from (D2-1) is combined with an extraction aid and distilled in such a way that the majority of the extraction aid and of the cyclohexane is drawn off via the bottom and the majority of the other compounds having a standard boiling point of 79 to 84° C. present in the top product from (D2-1) is drawn off from (D2-2) via the top,
  iii) a regeneration column (D2-3) in which the majority of the cyclohexane present in the bottom stream from (D2-2) is drawn off via the top and the majority of the extraction aid present in the bottom stream from (D2-2) is drawn off via the bottom, and
  iv) optionally a hydrogenation apparatus into which either stream (S3) or the top product from (D2-3) is conducted.

14. The process according to claim 13, wherein cyclohexane which originates from the distillation apparatus (D2) is combined with the cyclohexane which has been prepared in the isomerization in step a).

15. The process according to claim 1, wherein, in step b), cyclohexane is isolated in a purity of at least 98% by weight.

16. The process according to claim 15, wherein the purity is least 99.9% by weight.

17. The process according to claim 1, wherein the hydrocarbon mixture (HM2) comprising cyclohexane, MCP, possibly acyclic C5-C6-alkanes and possibly higher-boiling components than cyclohexane is fed into a distillation column (D4), and the majority of the MCP and, if present, of acyclic C5-C6-alkanes present in the feed to (D4) is removed from (D4) at a withdrawal point above the feed and recycled into or upstream of the isomerization in step a).

18. The process according to claim 17, wherein cyclohexane is drawn off from the distillation column (D4) in a purity of at least 98% by weight via the bottom of (D4) or via a side draw from (D4) below the feed.

19. The process according to claim 18, wherein the cyclohexane-enriched stream drawn off via the bottom of (D4) is introduced into a distillation column (D5), and a stream (S5) comprising higher-boiling components than cyclohexane is removed via the bottom of (D5) and cyclohexane is drawn off with a purity of at least 98% by weight via a takeoff point above the feed to (D5).

20. The process according to claim 18, wherein a cyclohexane-enriched stream is removed via the side draw from the distillation column (D4), the side draw being in the stripping section of (D4) or the cyclohexane-enriched stream from the side draw of (D4) being passed into an apparatus (D6) for further purification and cyclohexane being obtained therein via a takeoff point above the feed of (D6) with a purity of at least 98% by weight.

21. The process according to claim 20, wherein the apparatus (D6) is in the form of a distillation column and cyclohexane is obtained via the top of (D6).

22. The process according to claim 21, wherein the purity is at least 99.9% by weight.

23. The process according to claim 17, wherein the distillation column (D4) takes the form of a dividing wall column, the dividing wall is partly below the feed point, a draw point is in the region of the dividing wall and this draw point is used to withdraw a liquid cyclohexane stream having a purity of at least 98% by weight.

24. The process according to claim 1, wherein the catalyst used in step a) is an acidic ionic liquid, the acidic ionic liquid comprising, as a cation, an at least partly alkylated ammonium ion or a heterocyclic cation or, as an anion, a chloroaluminate ion having the composition $AlnCl(3n+1)$ where $1<n<2.5$.

25. The process according to claim 1, wherein the aromatics removal is an extractive benzene distillation, or the hydrocarbon mixture (HM1) has a lower concentration of aromatics than the feed stream (S1) to the apparatus for aromatics removal.

26. The process according to claim 1, additionally comprising step a-2), which is performed prior to step a) and prior to step a-1), comprising
  a-2) feeding the hydrocarbon mixture (HM1) into a distillation apparatus (D1),
    (HM1) comprising methylcyclopentane (MCP), at least one alkane having 7 or more carbon atoms and at least one aromatic,
    the at least one alkane having 7 or more carbon atoms being removed in (D1) from (HM1) to obtain the hydrocarbon mixture (HM1b), and
    (HM1b) comprising a reduced amount of at the least one alkane having 7 or more carbon atoms compared to (HM1), and (HM1b) being used rather than (HM1) in the subsequent steps a-1), a), and b).

27. A process for preparing cyclohexane, comprising the following steps:
  obtaining a hydrocarbon mixture (HM1) comprising benzene, methylcyclopentane (MCP) and at least one further compound selected from the group consisting of cyclohexane, cyclopentane, olefins and acyclic C5-C8-alkanes in an extractive benzene distillation connected downstream of a steamcracking process from a stream (S I) originating from the steamcracking process, wherein the hydrocarbon mixture (HM1) has a lower concentration of aromatics than the stream (S1);
  hydrogenating the hydrocarbon mixture (HM1) to obtain a hydrocarbon mixture (HM1a) having a reduced amount of benzene compared to (HM1);
  isomerizing the hydrocarbon mixture (HM1a) in the presence of an isomerization catalyst to obtain a hydrocarbon mixture (HM2) comprising cyclohexane, wherein the catalyst is an acidic ionic liquid, and
  isolating cyclohexane from the hydrocarbon mixture (HM2).

28. The process according to claim 27, wherein the acidic ionic liquid comprises, as a cation, an at least partly alkylated ammonium ion or a heterocyclic cation or, as an anion, a chloroaluminate ion having the composition $Al_nCl_{(3n+1)}$ where $1<n<2.5$.

* * * * *